United States Patent [19]

Kojima et al.

[11] 4,314,023
[45] Feb. 2, 1982

[54] PHOTOGRAPHIC SILVER HALIDE MATERIALS CONTAINING YELLOW COUPLER

[75] Inventors: Tamotsu Kojima, Kokubunji; Hiroyuki Imamura, Hachioji; Mitsuto Fujiwhara, Hachioji; Wataru Fujimatsu, Hachioji; Takaya Endo, Hino, all of Japan

[73] Assignee: Konishiroku Photo Industry Co., Ltd., Tokyo, Japan

[21] Appl. No.: 210,135

[22] Filed: Nov. 24, 1980

Related U.S. Application Data

[63] Continuation of Ser. No. 410,361, Oct. 29, 1973, abandoned, which is a continuation-in-part of Ser. No. 315,667, Dec. 15, 1972.

[30] Foreign Application Priority Data

Dec. 17, 1971 [JP] Japan .................................. 46-101848
Dec. 17, 1971 [JP] Japan .................................. 46-101850
Mar. 15, 1972 [JP] Japan .................................. 47-25754

[51] Int. Cl.³ .......................... G03C 7/00; G03C 1/40
[52] U.S. Cl. ..................................... 430/389; 430/472; 430/475; 430/476; 430/557; 430/558
[58] Field of Search ............... 430/475, 476, 557, 558, 430/389, 472

[56] References Cited

U.S. PATENT DOCUMENTS 3,730,722 5/1973 Inoue et al. ......................... 430/557

Primary Examiner—J. Travis Brown
Attorney, Agent, or Firm—Bierman & Bierman

[57] ABSTRACT

A photographic yellow coupler having a general formula selected from the group consisting of (I), (II) and (III)

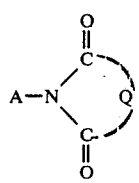

(I)

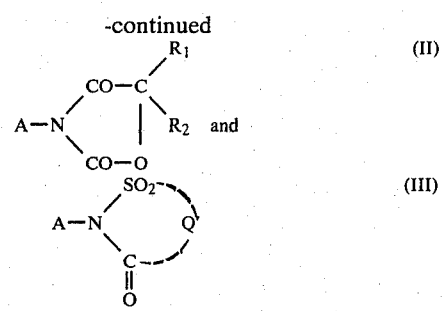

wherein A is a yellow coupler residue defined by removing one hydrogen atom of a active methylene group from a yellow coupler having the active methylene group; Q is a group having a formula selected from the group consisting of

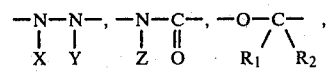

and

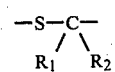

(where X and Y are individually a hydrogen atom or an alkyl, acyl, aryl or aralkyl group; Z is a hydrogen atom or an alkyl, aryl or aralkyl group; and $R_1$ and $R_2$ are individually a hydrogen atom or an alkyl, aryl or aralkyl group or both of $R_1$ and $R_2$ together may form a benzylidene group or a cycloalkyl group); and Q' is a group of the formula —$CH_2$—$CH_2$— or

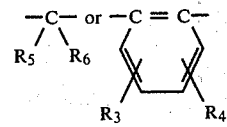

(wherein $R_3$ is a hydrogen or halogen atom or an alkoxy group; $R_4$ is a hydrogen or halogen atom, an amino, acylamino, ureido, lower alkyl, alkoxy or hydroxy group; and $R_4$ and $R_5$ are individually a lower alkyl group).

3 Claims, 1 Drawing Figure

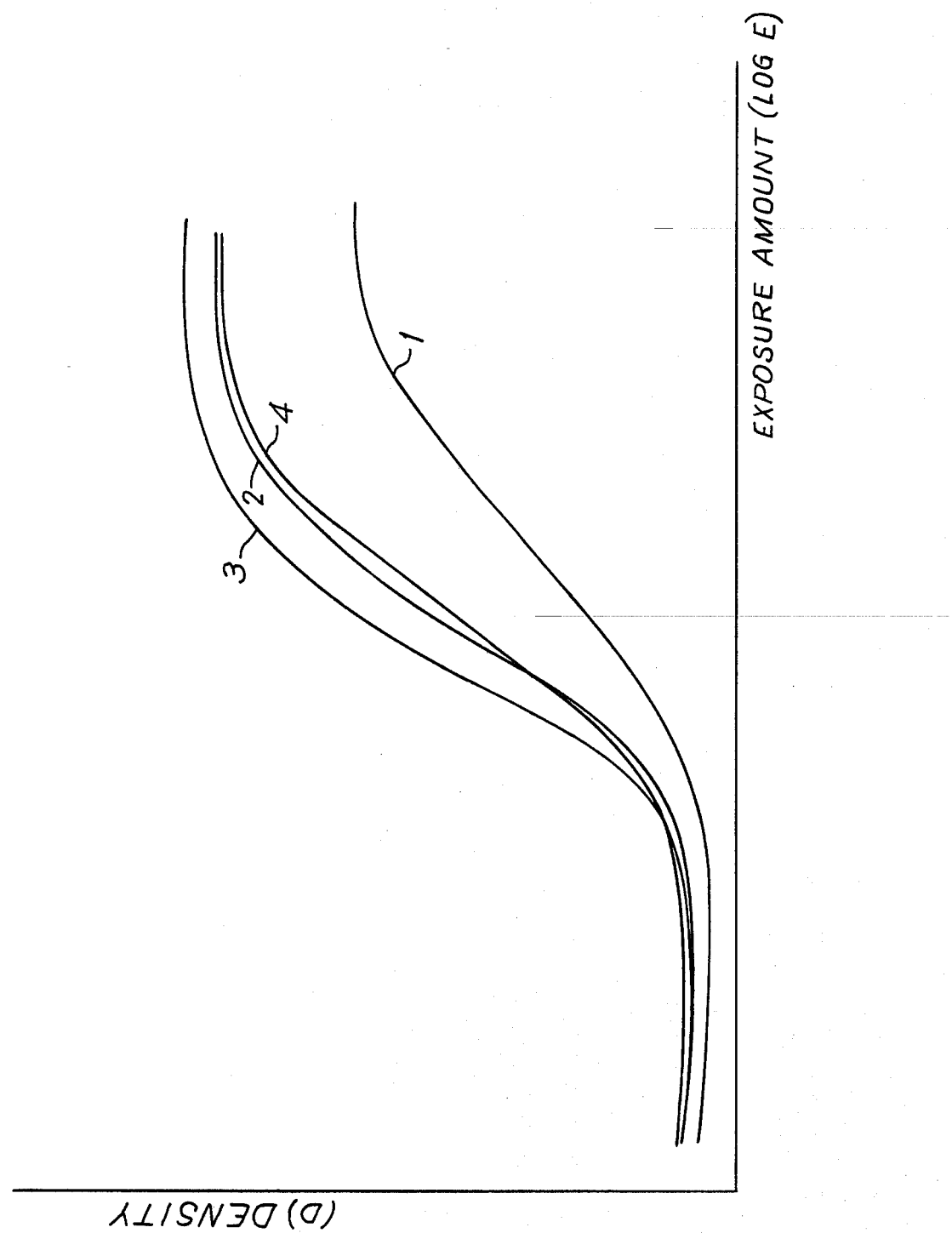

PHOTOGRAPHIC SILVER HALIDE MATERIALS CONTAINING YELLOW COUPLER

CROSS-REFERENCE TO RELATED APPLICATIONS

This application is a continuation of Application 410,361 filed Oct. 29, 1973 abandoned, which is a continuation-in-part of Application 315,667 filed Dec. 15, 1972, which, in turn, claims the priority of Japanese Application Nos. 101848/71 and 101850/71 filed Dec. 17, 1971 and Japanese Application No. 25754/72 filed Mar. 15, 1972.

BACKGROUND OF THE INVENTION

1. Field of the Invention

This invention relates to a novel coupler for forming a yellow image which is used in color photography.

2. Description of the Prior Art

It is well known that in color photography, a coupler-containing light-sensitive photographic material, for example, is exposed and then color developed with a developer containing an aromatic primary amine type developing agent as a main ingredient to form a dye image. Among the couplers used in said photography, the yellow coupler has an active methylene group which serves to form a yellow dye by coupling with an oxidation product of the aromatic primary amine type developing agent. In case the said active methylene group has not been substituted (i.e. in the case of an unsubstituted type yellow coupler), 4 molecules of silver halide is required in order to form one molecule of dye in the color development. Thus, the above-mentioned yellow coupler is called a 4-equivalent coupler.

On the other hand, it is well known that the same dye as in the case of unsubstituted type coupler can be formed also from a so-called substituted type yellow coupler, i.e. a coupler having an active methylene group, one of the hydrogen atoms of which has been substituted by such a substituent as a chlorine atom or the like halogen atom. In this case, the halogen atom or the like substituent is released in the course of color development reaction, and one molecule of dye can be formed from 2 molecules of developed silver halide. Such substituted type yellow coupler as mentioned above is called a 2-equivalent coupler. This 2-equivalent yellow coupler has, for example, such advantages over the 4-equivalent yellow coupler as mentioned below.

(1) The coupling rate can be more increased than in the case of the known 4-equivalent yellow coupler.

(2) The amount of silver halide required for forming a dye may be one half the amount required in the case of the 4-equivalent coupler, so that the production cost of photographic material can be reduced.

(3) The emulsion layer can be made thinner to improve the resulting color image in resolution and sharpness.

(4) In the case of a multi-layered photographic material, the transmission of light to the under layers is enhanced to improve the photographic speed of the photographic material.

Thus, the substituted type coupler is extremely advantageous for use in photography. On the other hand, however, the conventional substituted type coupler has any of such disadvantages that it tends to form fog or the like color stains and tends to disturb the development of photographic material.

In contrast to the conventional substituted type coupler, the substituted type coupler according to the present invention is colorless, is high in reactivity and scarcely forms color stains. Moreover, the yellow dye formed by the aforesaid color development is excellent in fastness to light, humidity and heat, has no unnecessary absorptions in the long wavelength region, shows less and sharp absorptions in the green light region, and has a color tone quite favorable for color reproduction.

SUMMARY OF THE INVENTION

Description of Preferred Embodiments

One class of the couplers according to the present invention is represented by the following general formula (I):

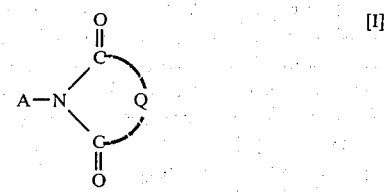

wherein A is a residue formed by removing one hydrogen atom of the active methylene group of a yellow image-forming coupler having an active methylene group; and Q is

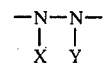

(where X and Y are individually a hydrogen atom or an alkyl, acyl, aryl or aralkyl group) or

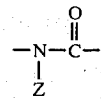

(where Z is a hydrogen atom or an alkyl, aryl or aralkyl group) or

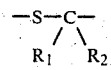

(where $R_1$ and $R_2$ are individually a hydrogen atom or an alkyl, aryl or aralkyl group or both of $R_1$ and $R_2$ may form together a benzylidene group or a cycloalkyl group).

The above-mentioned couplers (I) according to the present invention are characterized by having a substituent of the formula,

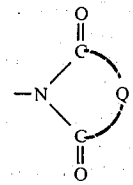

in the active point of the yellow coupler. Typical examples of the said substituent are such groups as mentioned below.

1-(2,5-Dioxo-1,3,4-triazolidinyl)
1-(3-Methyl-2,5-dioxo-1,3,4-triazolidinyl)
1-(3-Ethyl-2,5-dioxo-1,3,4-triazolidinyl)
1-(3-Phenyl-2,5-dioxo-1,3,4-triazolidinyl)
1-(3-Benzyl-2,5-dioxo-1,3,4-triazolidinyl)
1-(3,4-Dimethyl-2,5-dioxo-1,3,4-triazolidinyl)
1-[3-(m-Chlorophenyl)-2,5-dioxo-1,3,4-triazolidinyl]
1-[3-(p-chlorophenyl)-2,5-dioxo-1,3,4-triazolidinyl]
1-[3-(p-Tolyl)-2,5-dioxo-1,3,4-triazolidinyl]
1-(3-Methyl-4-phenyl-2,5-dioxo-1,3,4-triazolidinyl)
1-(3-Acetyl-2,5-dioxo-1,3,4-triazolidinyl)
1-(3-Acetyl-4-phenyl-2,5-dioxo-1,3,4-triazolidinyl)
1-(3,4-Diacetyl-2,5-dioxo-1,3,4-triazolidinyl)
1-(3-Ethyl-4-phenyl-2,5-dioxo-1,3,4-triazolidinyl)
1-[3-Propyl-4-(p-methoxyphenyl)-2,5-dioxo-1,3,4-triazolidinyl]
1-(3-Isopropyl-4-phenyl-2,5-dioxo-1,3,4-triazolidinyl)
1-(3-Butyl-4-phenyl-2,5-dioxo-1,3,4-triazolidinyl)
1-(3-Isoamyl-4-phenyl-2,5-dioxo-1,3,4-triazolidinyl)
1-(3-Cyclohexyl-2,5-dioxo-1,3,4-triazolidinyl)
1-[3-Benzyl-4-(m-acetylaminophenyl)-2,5-dioxo-1,3,4-triazolidinyl]
1-[3-Methyl-4-(p-bromophenyl)-2,5-dioxo-1,3,4-triazolidinyl]
1-[3-Methyl-4-(o-chlorophenyl)-2,5-dioxo-1,3,4-triazolidinyl]
1-[3-Phenyl-4-(o-chlorophenyl)-2,5-dioxo-1,3,4-triazolidinyl]
1-(3,4-Diphenyl-2,5-dioxo-1,3,4-triazolidinyl)
1-[3,4-Di-(o-chlorophenyl)-2,5-dioxo-1,3,4-triazolidinyl]
1-(3-Cyclohexyl-4-phenyl-2,5-dioxo-1,3,4-triazolidinyl)
1-[3-Cyclohexyl-4-(p-tolyl)-2,5-dioxo-1,3,4-triazolidinyl]
1-(3-Hexyl-4-phenyl-2,5-dioxo-1,3,4-triazolidinyl)
1-[3-(4-Methoxycyclohexyl)-4-phenyl-2,5-dioxo-1,3,4-triazolidinyl]
1-[3-(α-Methylbenzyl)-4-phenyl-2,5-dioxo-1,3,4-triazolidinyl]
1-(3-Nonyl-4-phenyl-2,5-dioxo-1,3,4-triazolidinyl)
1-(3,4-Diisobutyl-2,5-dioxo-1,3,4-triazolidinyl)
1-[3-Methyl-4-(2,5-dichlorophenyl)-2,5-dioxo-1,3,4-triazolidinyl]
1-(3-Ethyl-4-propyl-2,5-dioxo-1,3,4-triazolidinyl)
1-[3,4-Di-(p-tolyl)-2,5-dioxo-1,3,4-triazolidinyl]
1-(3-Allyl-4-phenyl-2,5-dioxo-1,3,4-triazolidinyl)
1-[3-(4-Biphenyl)-4-phenyl-2,5-dioxo-1,3,4-triazolidinyl]
1-(3-α-Naphthyl-2,5-dioxo-1,3,4-triazolidinyl)
1-(3-α-Naphthyl-4-methyl-2,5-dioxo-1,3,4-triazolidinyl)
1-(2,4,5-Trioxo-imidazolidinyl)
1-(3-Methyl-2,4,5-trioxo-imidazolidinyl)
1-(3-Ethyl-2,4,5-trioxo-imidazolidinyl)
1-(3-n-Butyl-2,4,5-trioxo-imidazolidinyl)
1-(3-iso-Acyl-2,4,5-trioxo-imidazolidinyl)
1-(3-n-Dodecyl-2,4,5-trioxo-imidazolidinyl)
1-(3-Phenyl-2,4,5-trioxo-imidazolidinyl)
1-(3-o-Chlorophenyl-2,4,5-trioxo-imidazolidinyl)
1-[3-(2,4-Dichlorophenyl)-2,4,5-trioxo-imidazolidinyl]
1-(3-p-Ethoxyphenyl-2,4,5-trioxo-imidazolidinyl
1-(3-o-Tolyl-2,4,5-trioxo-imidazolidinyl)
1-(3-m-Acetylaminophenyl-2,4,5-trioxo-imidazolidinyl)
1-(3-α-Naphthyl-2,4,5-trioxo-imidazolidinyl)
1-(3-Benzyl-2,4,5-trioxo-imidazolidinyl)
1-(3-Cyclohexyl-2,4,5-trioxo-imidazolidinyl)
1-(3-p-Nitrophenyl-2,4,5-trioxo-imidazolidinyl)
1-(3-p-Bromophenyl-2,4,5-trioxo-imidazolidinyl)

Another class of couplers according to the present invention is represented by the following general formula (II):

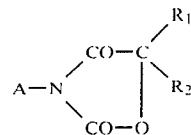

wherein A is a residue formed by removing one hydrogen atom of the active methylene group of a yellow coupler having an active methylene group; and $R_1$ and $R_2$ are individually a hydrogen atom or an alkyl, aryl, aralkyl, cycloalkyl, benzylidene or carboxyl group, provided that $R_2$ may be removed and $R_1$ may form a benzylidene group by bonding through a double bond to the carbon to which $R_1$ is bonded.

The above-mentioned couplers II according to the present invention are characterized by having in the active point thereof a substituent of the formula,

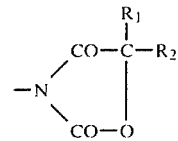

Typical examples of the said substituent are such groups as mentioned below.

2,4-Oxazolidinedione
5-Methyl-2,4-oxazolidinedione
5,5-Diethyl-2,4-oxazolidinedione
5-Phenyl-2,4-oxazolidinedione
5-Benzyl-5-methyl-2,4-oxazolidinedione
5,5-Dimethyl-2,4-oxazolidinedione
5-n-Butyl-5-methyl-2,4-oxazolidinedione
5,5-Diisopropyl-2,4-oxazolidinedione
5-Phenyl-5-n-propyl-2,4-oxazolidinedione
5-Phenyl-5-ethyl-2,4-oxazolidinedione
5,5-Diphenyl-2,4-oxazolidinedione
5-Phenyl-5-isobutyl-2,4-oxazolidinedione
5-n-Hexyl-5-methyl-2,4-oxazolidinedione
5-(p-Methoxyphenyl)-5-methyl-2,4-oxazolidinedione
5-Isopropyl-2,4-oxazolidinedione
5-Methyl-5-ethyl-2,4-oxazolidinedione
5-Cyclopentyl-5-carbon-2,4-oxazolidinedione 5-n-Heptyl-5-methyl-2,4-oxazolidinedione
5,5-Di-n-amyl-2,4-oxazolidinedione
5-Isobutyl-5-phenyl-2,4-oxazolidinedione
5-Cyclohexyl-2,4-oxazolidinedione
5-Benzylidene-2,4-oxazolidinedione
5-Nonyl-5-methyl-oxazolidinedione
5-(p-Chlorobenzyl)-oxazolidinedione Class I and II yellow couplers, in which the above-mentioned substituents have been substituted in the active points thereof, can be any of those which have active methylene groups in the molecules. When these substituents are substituted in the active points of couplers, such excellent properties as mentioned previously are imparted to the couplers.

Typical examples of the couplers (I) according to the present invention which have the above-mentioned substituents are shown below, but the couplers of this invention are not limited to these.

1 Exemplified couplers (1)  α-Pivalyl-α-[1-(2,5-dioxo-1,3,4-triazolidinyl)]-acetanilide

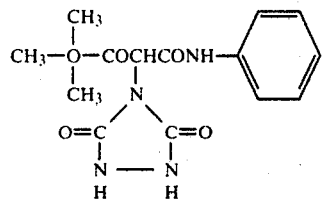

(2)  α-Pivalyl-α-[1-(3,4-diphenyl-2,5-dioxo-1,3,4-triazolidinyl)]-2,5-dichloroacetanilide

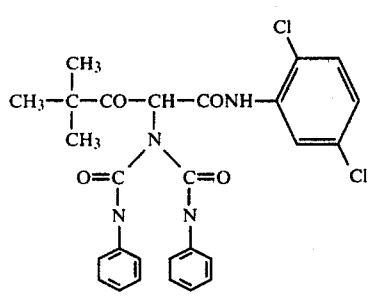

(3)  α-Benzoyl-α-[1-(2,4,5-trioxo-imidazolidinyl)]-acetanilide

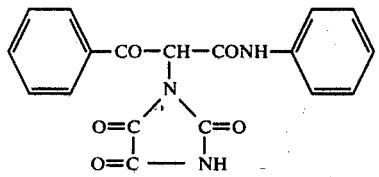

(4)  α-Pivalyl-α-[1-(3-methyl-4-phenyl-2,5-dioxo-1,3,4-triazolidinyl)]-acetanilide

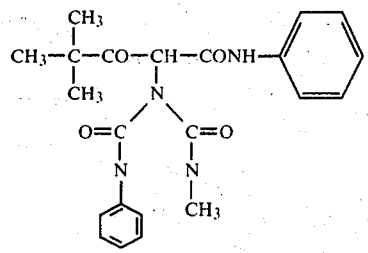

(5)  α-Pivalyl-α-[1-(3-phenyl-2,4,5-trioxoimidazolidinyl)]-acetanilide

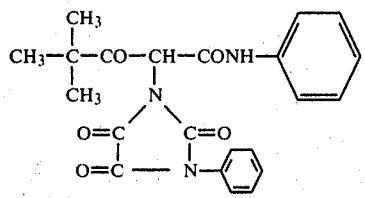

(6)  α-Benzoyl-α-[1-{3-(2,4-dimethyl-6-chlorophenyl)-2,5-dioxo-1,3,4-triazolidinyl}]-acetanilide

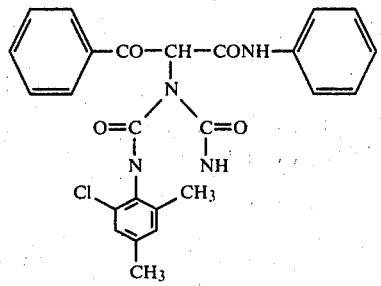

(7)  α-Pivalyl-α-[1-(3-methyl-4-phenyl-2,5-dioxo-1,3,4-triazolidinyl)]-2-chloro-5-[γ-(2,4-di-t-acylphenoxy)-butyramido]-acetanilide

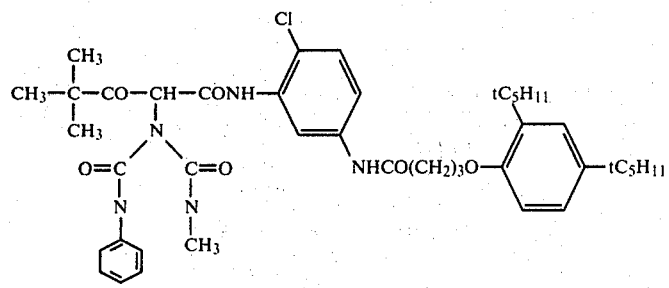

(8)  α-Pivalyl-α-[1-(3-acetyl-4-phenyl-2,5-dioxo-1,3,4-triazolidinyl)]-acetanilide

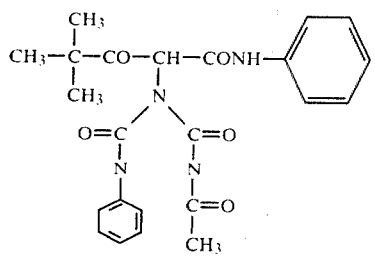

(9) α-[3-{α-(2,4-Di-t-amylphenoxy)-butyramido}-benzoyl]-α-[1-(3-methyl-2,4,5-trioxoimidazolidinyl)]-2-methoxy-acetanilide

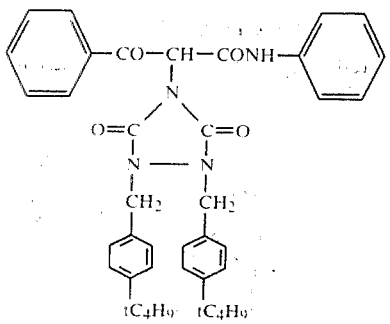

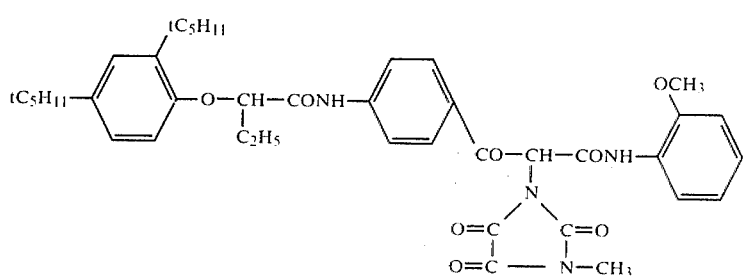

(10) α-Pivalyl-α-[1-(3,4-diacetyl-2,5-dioxo-1,3,4-triazolidinyl)]-acetanilide

(12) α-Pivalyl-α-[1-(3,4-diphenyl-2,5-dioxo-1,3,4-triazolidinyl)]-2-chloro-5-[γ-(2,4-di-t-amylphenoxy)-butyramido]-acetanilide

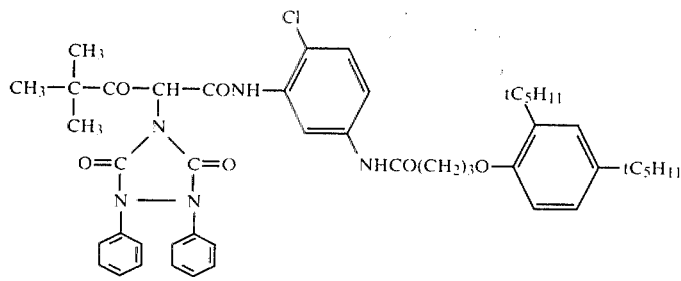

(13) α-(α-Dodecyloxybenzoyl)-α-[1-(3,4-dimethyl-2,5-dioxo-1,3,4-triazolidinyl)]-3,5-dicarboxyacetanilide-di-potassium salt

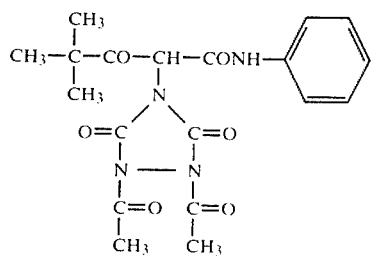

(11) α-Benzoyl-α-[1-{3,4-di-(p-t-butylbenzyl)-2,5-dioxo-1,3,4-triazolidinyl}]-acetanilide

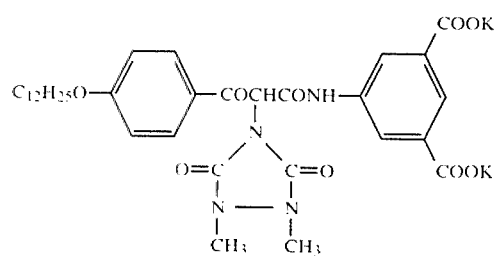

(14) α-Pivalyl-α-[1-(3-n-dodecyl-2,4,5-trioxoimidazolidinyl)]-acetanilide

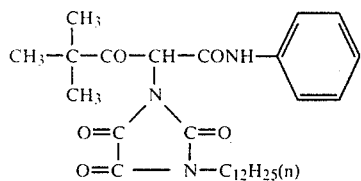

(15) α-Pivalyl-α-[1-(3,4-di-o-chlorophenyl-2,5-dioxo-1,3,4-triazolidinyl)]-2-chloro-5-[γ-(2,4di-t-amylphenoxy)-butyramido]-acetanilide

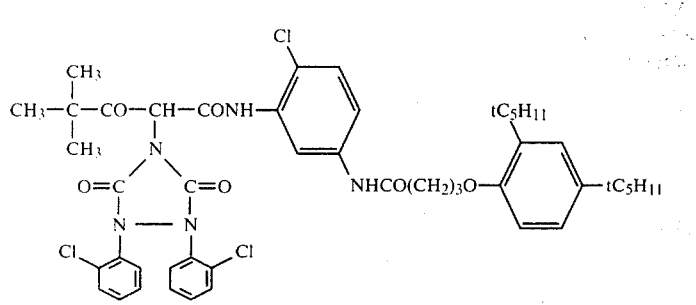

(16) α-(3-Palmitoylamidobenzoyl)-α-[1-(3-p-methoxyphenyl-2,4,5-trioxo-imidazolidinyl)]-2-methoxy-5-carboxyacetanilide-potassium salt

(17) α-Pivalyl-α-[1-(3-methyl-2,5'-dioxo-1,3,4-triazolidinyl)]-acetanilide

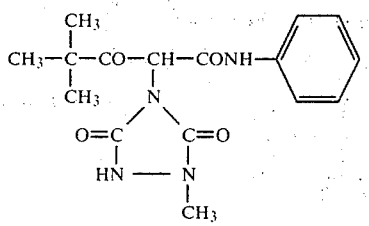

(18) α-Benzoyl-α-[1-(3-p-chlorophenyl-4-p-methylbenzyl-2,5-dioxo-1,3,4-triazolidinyl)]-2-chloro-5-[α-(2,4-di-t-amylphenoxy)-butyramide]-acetanilide

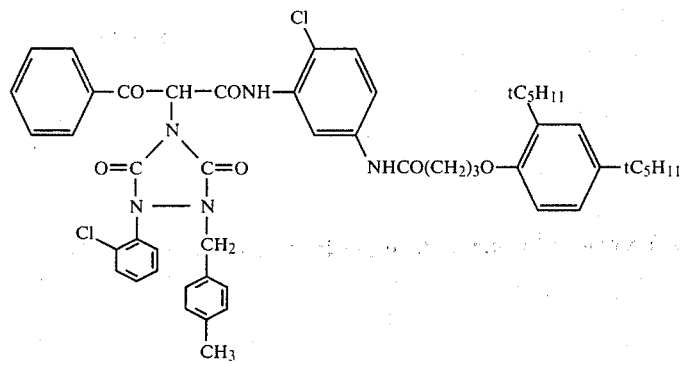

(19) α-Pivalyl-α-[1-(3-benzyl-2,4,5-trioxoimidazolidinyl)]-2-chloro-5-[γ-(2,4-di-t-amylphenoxy)-butyramide]-acetanilide

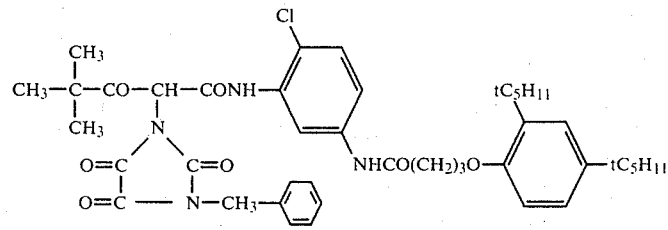

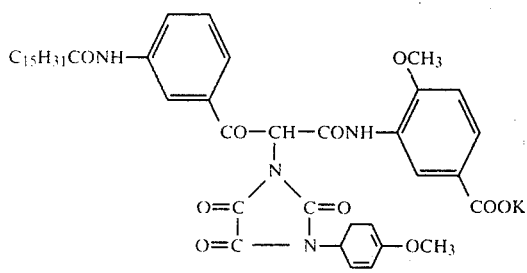

(20) α-Pivalyl-α-[1-(3-methyl-4-phenyl-2,5-dioxo-1,3,4-triazolidinyl)]-2-chloro-5-(n-dodecyloxycarbonylmethoxycarbonyl)-acetanilide

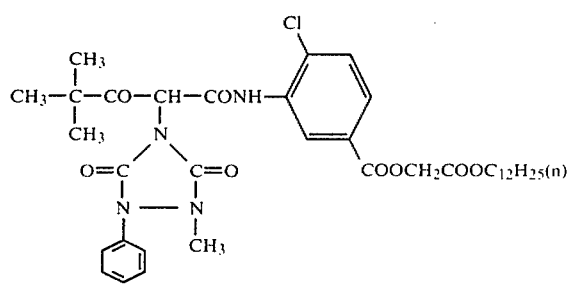

(21) α-Pivalyl-α-[1-(3-o-chlorophenyl-2,4,5-trioxoimidazolidinyl)]-2-chloro-5-[α,α,α-(dimethyl-n-dodecyloxycarbonyl)-methoxycarbonyl]-acetanilide

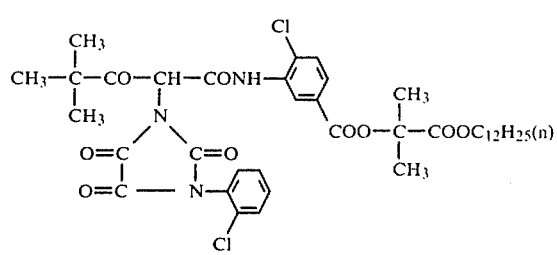

(22) α-(2,4-Thiazolidineone)-α-pivalyl-acetanilide

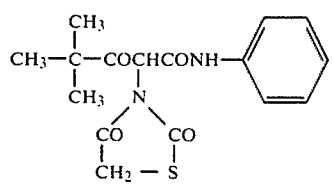

(23) α-(2,4-Thiazolidineone)-α-benzoyl-acetanilide

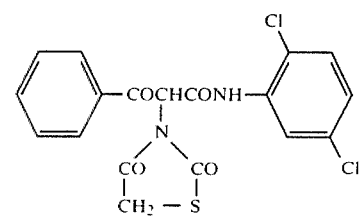

(24) α-(5-Methyl-2,4-thiazolidineone)-α-pivalyl-acetanilide

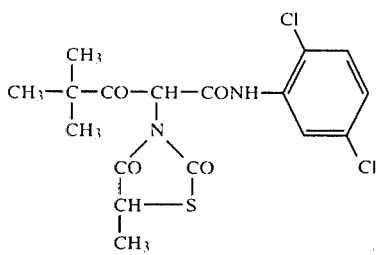

(25) α-(5-Methyl-2,4-thiazolidineone)-α-pivalyl-2-chloro-5-[γ-(2,4-di-t-amylphenoxy)-butylamide]-acetanilide

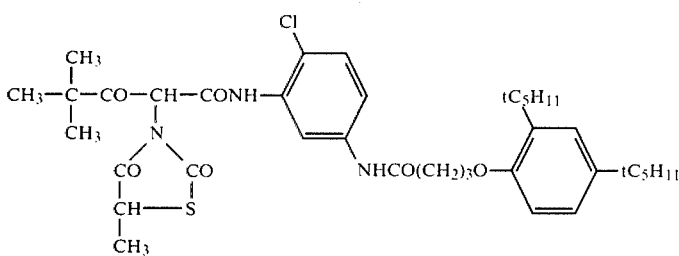

(26) α-(5-Phenyl-2,4-thiazolidineone)-α-pivalyl-5-[γ-(2,4-di-t-amylphenoxy)-butylamide]-acetanilide

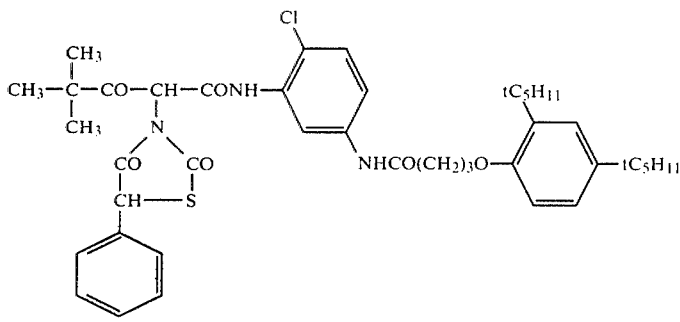

(27) α-(2,4-Thiazolidineone)-α-{3-[α-2,4-di-t-amylphenoxy)-butylamide]-benzoyl}-2-methoxyacetanilide

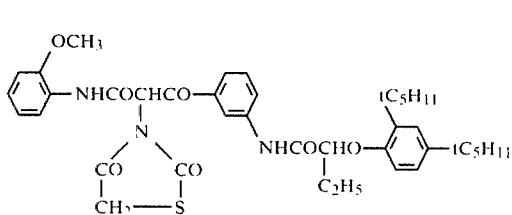

(28) α-(5-Benzyl-2,4-thiazolidineone)-α-benzoylacetanilide

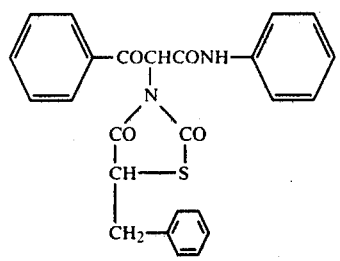

(29) α-(5,5-Dimethyl-2,4-thiazolidineone)-α-pivalyl-2,5-dichloroacetanilide

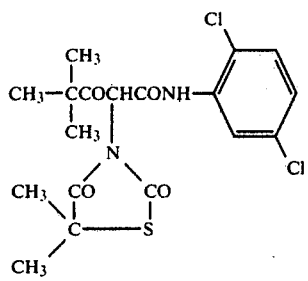

(30) α-5-(p-Chloro-phenyl-2,4-thiazolidineone)-α-(p-octadecyl-oxybenzoyl)-3,5-dicarboxyacetanilide dipotassium salt

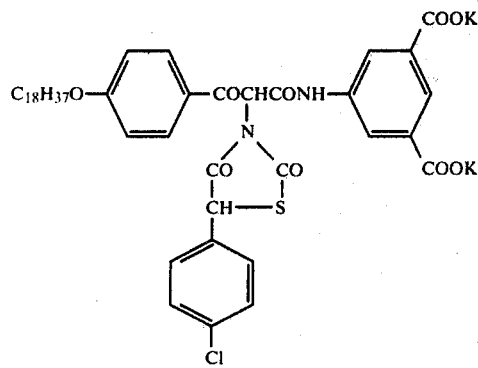

(31) α-(5,5-Diphenyl-2,4-thiazolidineone)-α-pivalylacetanilide

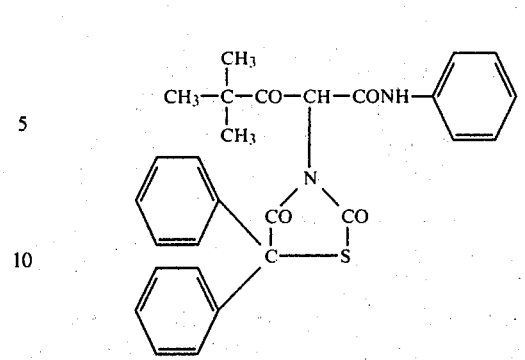

(32) α-{5-(p-Chloro-benzylidene)-2,4-thiazolidineone}-α-benzoylacetanilide

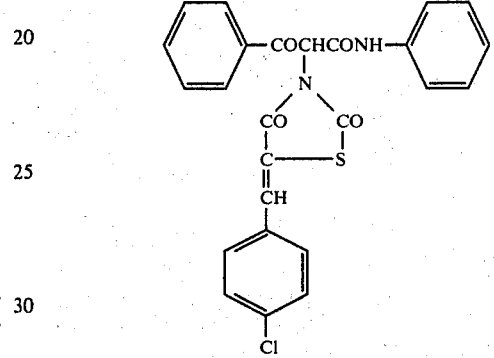

(33) α-(5-Ethyl-5-phenyl-2,4-thiazolidineone)-α-pivalyl-2-chloro-5-[γ-(2,4-di-t-amylphenoxy)-butylamide]-acetanilide

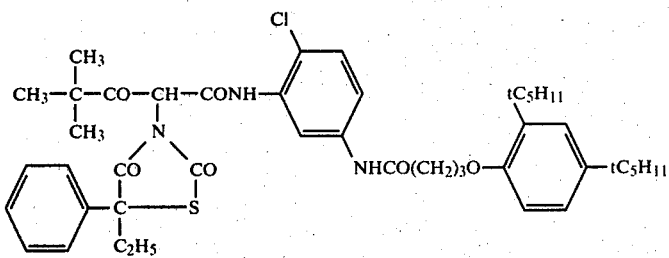

(34) α-(5-n-Pentyl-2,4-thiazolidineone)-α{3-[α-2,4-di-t-amylphenoxy)-butylamid]-benzoyl}-2-methoxyacetanilide.

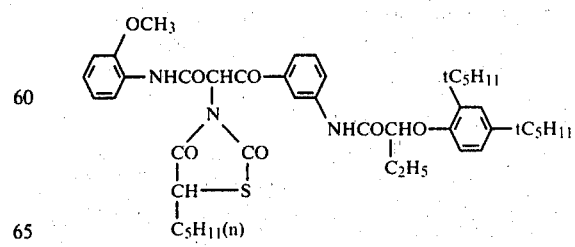

(35) α-(5,5-di-n-Pentyl-2,4-thiazolidineone)-α-pivalylacetanilide

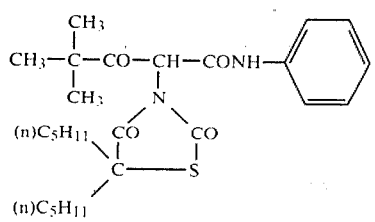

(36) α-(2,4-Thiazolidineone)-α-pivalyl-2-chloro-5-[γ-(2,4-di-t-amylphenoxy)-butylamide]-acetanilide

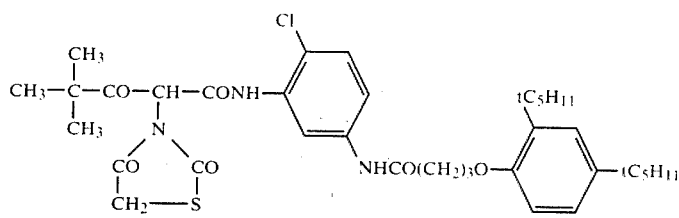

Typical examples of the couplers II according to the present invention are shown below, but the couplers of this invention are not limited to these.

(37) α-(2,4-Oxazolidinedione)-α-pivalyl-acetanilide

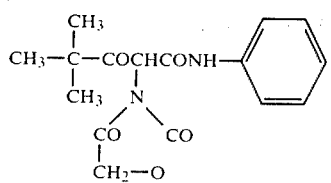

(38) α-(5-Methyl-2,4-oxazolidinedione)-α-pivalyl-acetanilide

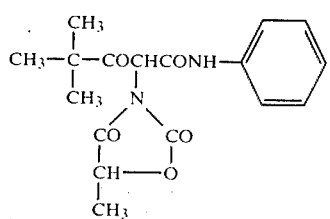

(39) α-(2,4-Oxazolidinedione)-2-pivalyl-2-chloro-5-[γ-(2,4-di-t-amylphenoxy)-butyramide]-acetanilide

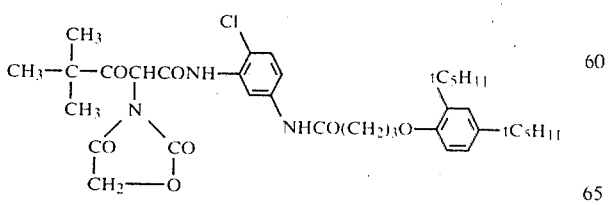

(40) α-(5-Phenyl-2,4-oxazolidinedione)-α-pivalyl-acetanilide

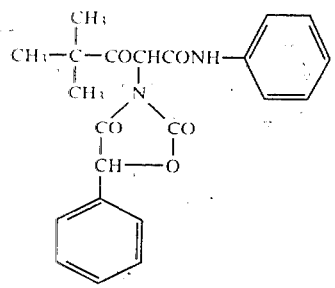

(41) α-(2,4-Oxazolidinedione)-αbenzoyl-acetanilide

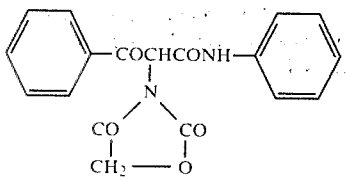

(42) α-(5-Dimethyl-2,4-oxazolidinedione)-αbenzoyl-acetanilide

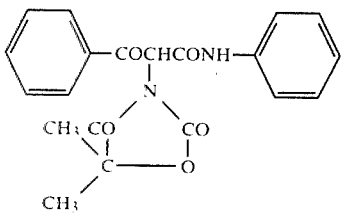

(43) α-(5-Benzyl-2,4-oxazolidinedione)-α-pivalyl-2-chloro-5-[γ-(2,4-di-t-amylphenoxy)-butyramide]-acetanilide

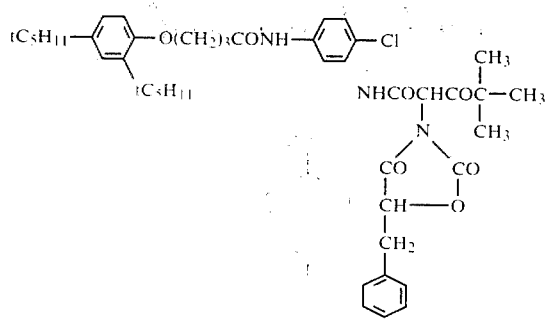

(44) α-(5-n-Butyl-5-methyl-2,4-oxazolidinedione)-α-pivalyl-acetanilide

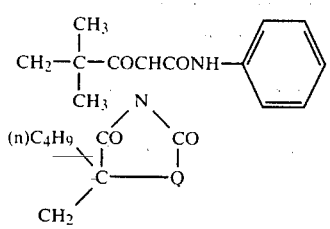

(45) α-(5-Phenyl-2,4-oxazolidinedione)-α-{3-[α-(2,4-di-t-amylphenoxy)-butyramide]-benzoyl}-2-methoxy-acetanilide

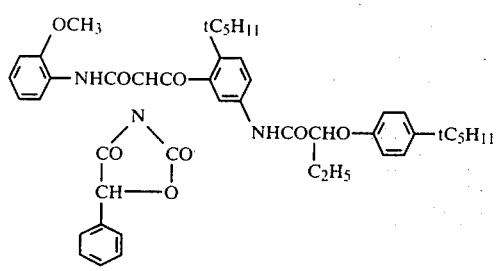

(46) α-(5-Methyl-2,4-oxazolidinedione)-α-pivalyl-2-chloro-5-[γ-(2,4-di-t-amylphenoxy)-butyramide]-acetanilide

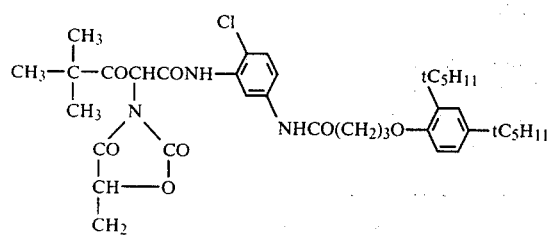

(47) α-(5-Isopropyl-2,4-oxazolidinedione)-α-pivalyl-2,5-dichloro-acetanilide

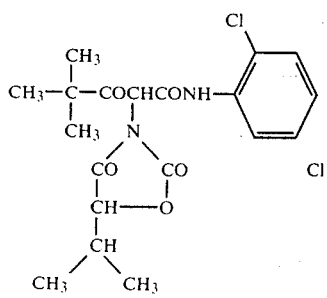

(48) α-(5,5-Diphenyl-2,4-oxazolidinedione)-α-benzoyl-acetanilide

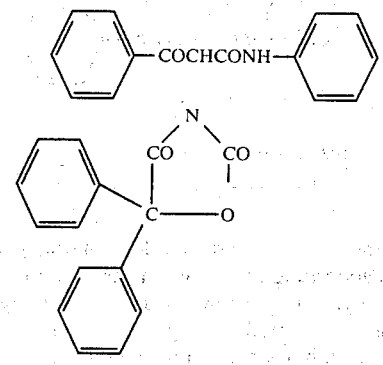

(49) α-(5-Benzyl-5-methyl-2,4-oxazolidinedione)-α-pivalyl-2-chloro-5-[γ-(2,4-di-t-amylphenoxy)-butyramide]-acetanilide

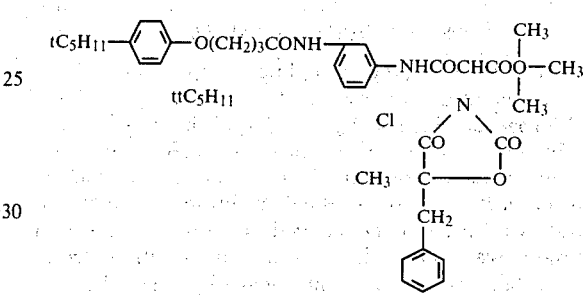

(50) α-(5-Phenyl-2,4-oxazolidinedione)-α-pivalyl-2-chloro-5-[γ-(2,4-di-t-amylphenoxy)-butyramide]-acetanilide

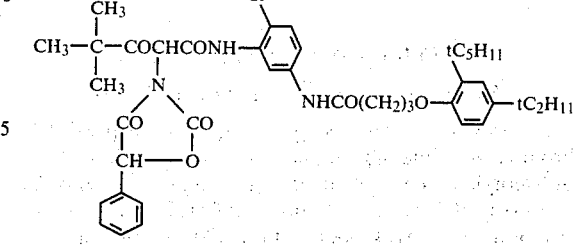

(51) α-5,5-Dimethyl-2,4-oxazolidinedione)-α-(p-octadecylosybenzoyl)-3,5-dicarboxyacetanilide-dipotassium salt

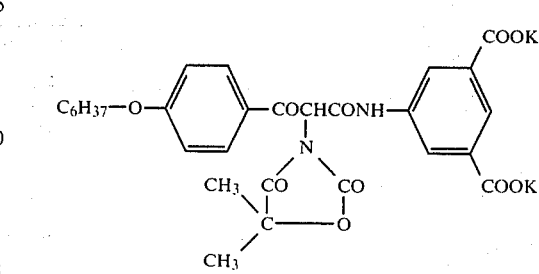

(52) α-(5-Methyl-5-nonyl-2,4-oxazolidinedione)-α-pivalyl-acetanilide

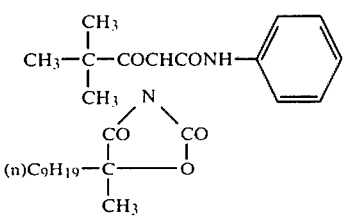

The above-mentioned couplers of the general formula (I) according to the present invention can be synthesized by, for example, reacting a yellow coupler having an active methylene group, one of the hydrogen atoms of which has been substituted by a halogen atom, with a substituted or unsubstituted urazol or parabanic acid.

Typical procedures for synthesizing the couplers of this class according to the present invention are explained in detail below with reference to synthesis examples.

SYNTHESIS EXAMPLE 1

Cl Synthesis of the exemplified coupler (2)

A mixture comprising 6.4 g. of α-pivalyl-α-chloroacetanilide and 6 g. of 1,2-diphenyl urazol potassium salt was reacted by heating under reflux for 3 hours in 100 ml. of acetonitrile. After the reaction, the reaction liquid was subjected to filtration, and the filtrate was dried under reduced pressure. The resulting residue was recrystallized from 40 ml. of ethyl alcohol to obtain 5.5 g. of white scale-like crystals, m.p. 167°–169° C.

Elementary analysis:

|  | C | H | N | Cl |
|---|---|---|---|---|
| Calculated (%) | 60.11 | 4.48 | 10.38 | 13.14 |
| Found (%) | 60.15 | 4.51 | 10.14 | 13.03 |

SYNTHESIS EXAMPLE 2

Synthesis of the exemplified coupler (5)

A mixture comprising 6 g. of α-pivalyl-α-bromoacetanilide, 4 g. of phenyl-parabanic acid and 3 g. of triethylamine was reacted by heating under reflux for 3 hours in 100 ml. of acetonitrile. After the reaction, the reaction liquid was poured into 300 ml. of water to deposit precipitates. The precipitates were recovered by filtration and dried, and the resulting crystals were recrystallized from 100 ml. of ethyl alcohol to obtain 4 g. of white needle-like crystals, m.p. 248°–249° C.

Elementary analysis:

|  | C | H | N |
|---|---|---|---|
| Calculated (%) | 64.85 | 5.20 | 10.31 |
| Found (%) | 64.09 | 5.17 | 10.07 |

SYNTHESIS EXAMPLE 3

Synthesis of the exemplified coupler (7)

A mixture comprising 60 g. of α-pivalyl-α-chloro-2-chloro-5-[γ-(2,4-di-t-amylphenoxy)-butyramido]-acetanilide and 27 g. of 1-methyl-2-phenylurazol potassium salt was reacted by heating under reflux for 4 hours in 500 ml. of acetonitrile. After the reaction, the reaction liquid was poured into 1 liter of water to deposit precipitates. The precipitates were recovered by filtration and dried, and the resulting crystals were recrystallized from 400 ml. of a 5:1 mixture of n-hexane and alcohol to obtain 53 g. of white powdery crystals, m.p. 158°–160° C.

Elementary analysis:

|  | C | H | N | Cl |
|---|---|---|---|---|
| Calculated (%) | 67.58 | 7.29 | 7.50 | 4.75 |
| Found (%) | 67.50 | 7.35 | 7.44 | 4.61 |

SYNTHESIS EXAMPLE 4

Synthesis of the exemplified coupler (15)

A mixture comprising 12 g. of α-pivalyl-α-chloro-2-chloro-5-[γ-(2,4-di-t-amylphenoxy)-butyramide]-acetanilide and 8.0 g. of 1,2-di-o-chlorophenylurazol potassium salt was reacted by heating under reflux for 4 hours in 120 ml. of acetonitrile. After the reaction, the reaction liquid was subjected to filtration, and the filtrate was dried under reduced pressure. The resulting residue was recrystallized from 150 cc. of a 5:1 mixture of n-hexane and alcohol to obtain 13.6 g. of white powdery crystals, m.p. 135°–137° C.

Elementary analysis:

|  | C | H | N | Cl |
|---|---|---|---|---|
| Calculated (%) | 63.33 | 6.10 | 7.85 | 11.93 |
| Found (%) | 63.41 | 6.00 | 7.80 | 12.12 |

According the above-mentioned synthesis procedures, other exemplified couplers (1) through (21) can be synthesized as well. Elementary analysis values of the thus synthesized couplers are as set forth in the following table:

| Exemplified Compound No. | Calculated (%) | | | | | Found (%) | | | | |
|---|---|---|---|---|---|---|---|---|---|---|
|  | C | H | N | Cl | K | C | H | N | Cl | K |
| (1) | 56.59 | 5.70 | 17.60 | — | — | 56.40 | 5.77 | 17.75 | — | — |
| (3) | 61.54 | 3.73 | 11.96 | — | — | 61.32 | 3.90 | 11.79 | — | — |
| (4) | 64.69 | 5.92 | 13.72 | — | — | 64.60 | 6.13 | 13.70 | — | — |
| (6) | 62.95 | 4.43 | 11.74 | 7.43 | — | 63.17 | 4.40 | 11.54 | 7.21 | — |
| (8) | 63.29 | 5.54 | 12.84 | — | — | 63.29 | 5.50 | 12.71 | — | — |
| (9) | 67.39 | 6.79 | 7.86 | — | — | 67.11 | 6.75 | 9.86 | — | — |
| (10) | 56.71 | 5.51 | 13.92 | — | — | 56.90 | 5.44 | 13.78 | — | — |
| (11) | 74.26 | 6.71 | 8.88 | — | — | 74.49 | 6.52 | 8.67 | — | — |
| (12) | 68.63 | 6.86 | 8.51 | 4.31 | — | 68.60 | 6.74 | 8.61 | 4.33 | — |
| (13) | 53.69 | 5.86 | 8.14 | — | 11.36 | 53.78 | 5.95 | 7.99 | — | 11.54 |
| (14) | 67.31 | 8.27 | 8.41 | — | — | 67.43 | 8.50 | 8.15 | — | — |
| (16) | 62.73 | 6.24 | 6.80 | — | 4.75 | 62.57 | 6.40 | 6.77 | — | 4.92 |

-continued

| Exemplified | Calculated (%) | | | | | Found (%) | | | | |
|---|---|---|---|---|---|---|---|---|---|---|
| Compound No. | C | H | N | Cl | K | C | H | N | Cl | K |
| (17) | 52.32 | 6.07 | 13.86 | — | — | 57.71 | 6.07 | 16.85 | — | — |
| (18) | 67.68 | 6.12 | 7.74 | 7.83 | — | 67.55 | 6.10 | 7.82 | 7.94 | — |
| (19) | 66.77 | 6.90 | 7.24 | 4.58 | — | 66.85 | 7.06 | 7.23 | 4.44 | — |
| (20) | 62.30 | 6.92 | 7.57 | 4.97 | — | 62.29 | 6.95 | 7.56 | 4.77 | — |
| (21) | 60.45 | 6.37 | 5.42 | 9.15 | — | 60.40 | 6.45 | 5.53 | 9.01 | — |

SYNTHESIS EXAMPLE 5

Synthesis of the exemplified coupler (1)

A mixture comprising 2.5 g. of α-pivalyl-α-chloroacetanilide and 1.99 g. of 2,4-thiazolidineone potassium salt was reacted by heating under reflux for 2 hours in 30 ml. of acetonitrile. After the reaction, the reaction liquid was filtered, and the filtrate was dried under reduced pressure. The resulting residue was recrystallized from ethyl acetate to obtain white crystals, m.p. 196.5°–199.5° C.

Elementary analysis:

| | C | H | N | S |
|---|---|---|---|---|
| Calculated (%) | 57.47 | 5.43 | 8.38 | 32.06 |
| Found (%) | 57.61 | 5.41 | 8.29 | 31.99 |

According to the above-mentioned synthesis procedures, other exemplified couplers (22) to (36) can be synthesized as well. Elementary analysis of the thus synthesized couplers are set forth in the following table.

| Exemplified | Calculated (%) | | | | | Found (%) | | | | |
|---|---|---|---|---|---|---|---|---|---|---|
| Compound No. | C | H | N | S | Cl | C | H | N | S | Cl |
| (23) | 51.07 | 2.86 | 6.62 | 7.57 | 16.75 | 51.21 | 2.81 | 6.71 | 7.41 | 16.63 |
| (24) | 48.93 | 4.35 | 6.71 | 7.68 | 16.99 | 49.01 | 4.40 | 6.71 | 7.74 | 17.00 |
| (25) | 64.56 | 7.32 | 6.10 | 4.66 | 5.15 | 64.50 | 7.31 | 6.18 | 4.80 | 5.10 |
| (26) | 67.22 | 6.99 | 5.60 | 4.27 | 4.73 | 67.11 | 7.00 | 5.65 | 4.41 | 4.67 |
| (27) | 64.93 | 9.11 | 6.31 | 4.82 | — | 65.02 | 9.20 | 6.25 | 4.90 | — |
| (28) | 67.55 | 4.54 | 6.30 | 7.21 | — | 67.51 | 4.53 | 6.32 | 7.15 | — |
| (29) | 50.12 | 4.67 | 6.50 | 7.43 | 16.44 | 50.01 | 4.67 | 6.49 | 7.40 | 16.34 |
| (30) | 58.80 | 5.83 | 3.12 | 3.57 | 3.95 | 58.65 | 5.79 | 3.10 | 3.51 | 3.91 |
| (31) | 69.11 | 5.39 | 5.76 | 6.59 | — | 69.23 | 5.38 | 5.65 | 6.62 | — |
| (32) | 62.95 | 3.59 | 5.87 | 6.72 | 7.44 | 63.02 | 4.00 | 5.75 | 6.64 | 7.36 |
| (33) | 66.85 | 7.16 | 5.32 | 4.06 | 4.49 | 66.91 | 7.16 | 5.23 | 4.01 | 4.43 |
| (34) | 66.90 | 7.81 | 5.71 | 4.36 | — | 66.82 | 7.79 | 5.74 | 4.27 | — |
| (35) | 65.86 | 8.07 | 5.90 | 6.74 | — | 65.81 | 8.05 | 5.87 | 6.69 | — |
| (36) | 63.00 | 7.05 | 6.12 | 4.67 | 5.17 | 63.12 | 7.03 | 6.21 | 4.59 | 5.24 |

The above-mentioned couplers of the general formula (II) according to the present invention can be synthesized by, for example, reacting a yellow coupler having an active methylene group, one of the hydrogen atoms of which has been substituted by a halogen atom, with a substituted or unsubstituted 2,4-oxazolidinedione.

Typical procedures for synthesizing the couplers of this class according to the present invention are explained in detail below with reference to the following synthesis examples.

SYNTHESIS EXAMPLE 6

Synthesis of the exemplified coupler (37)

A mixture comprising 7.6 g. of α-pivalyl-α-chloroacetanilide and 5 g. of 2,4-oxazolidinedione potassium salt was reacted by heating under reflux for 5 hours in 100 ml. of acetonitrile. After the reaction, the reaction liquid was subjected to filtration, and the filtrate was dried under reduced pressure. Thereafter, the residue was recrystallized from ethyl alcohol to obtain white crystals, m.p. 230°–231° C.

Elementary analysis:

| | C | H | N |
|---|---|---|---|
| Calculated (%) | 60.37 | 5.70 | 8.80 |
| Found (%) | 60.09 | 5.69 | 8.89 |

SYNTHESIS EXAMPLE 7

Synthesis of the exemplified coupler (41)

A mixture comprising 5.2 g. of α-benzoyl-α-chloroacetanilide and 3.2 g. of 2,4-oxazolidinedione potassium salt was reacted by heating under reflux for 4 hours in 70 ml. of acetonitrile. After the reaction, the reaction liquid was subjected to filtration, and the filtrate was dried under reduced pressure. Thereafter, the residue was dissolved in 50 ml. of ethyl acetate, and then extracted with 100 ml. of a 5% aqueous solution of sodium carbonate, and the alkali layer was neutralized with dilute hydrochloric acid. This neutralized liquid was extracted with 100 ml. of ethyl acetate, and the ethyl acetate layer was concentrated. Subsequently, the residue was recrystallized from benzene to obtain white powdery crystals, m.p. 187°–188° C.

Elementary analysis:

| | C | H | N |
|---|---|---|---|
| Calculated (%) | 63.90 | 4.17 | 8.28 |
| Found (%) | 64.01 | 4.12 | 8.39 |

SYNTHESIS EXAMPLE 8

Synthesis of the exemplified coupler (46)

A mixture comprising 5 g. of α-pivalyl-α-chloro-2-chloro-5-[γ-(2,4-di-t-amylphenoxy)-butyramido]-acetanilide and 1 g. of 5-methyl-2,4-oxazolidinedione potassium salt was reacted under reflux for 5 and half hours in 100 ml. of acetonitrile. After the reaction, the reaction liquid was subjected to filtration, and the filtrate was dried under reduced pressure. Thereafter, the residue was washed 2 times with n-hexane at an elevated temperature, and the resulting oily substance was recrystallized from a solvent comprising n-hexane and ethyl alcohol to obtain white powdery crystals, m.p. 174°–175° C.

Elementary analysis:

|  | C | H | N | Cl |
|---|---|---|---|---|
| Calculated (%) | 64.94 | 7.47 | 6.14 | 5.18 |
| Found (%) | 64.19 | 7.42 | 6.31 | 5.23 |

SYNTHESIS EXAMPLE 9

Synthesis of the exemplified coupler (50)

A mixture comprising 4.8 g. of α-pivalyl-α-chloro-2-chloro-5-[γ-(2,4-di-t-amylphenoxy)-butyramido]-acetanilide and 1.8 g. of 5-phenyl-2,4-oxazolidinedione potassium salt was reacted under reflux for 2 hours in 100 ml. of acetonitrile. After the reaction, the reaction liquid was subjected to filtration, and the filtrate was dried under reduced pressure. Thereafter, the residue was recrystallized from a solvent comprising n-hexane and methanol to obtain white powdery crystals, m.p. 169°–171° C.

Elementary analysis:

|  | C | H | N | Cl |
|---|---|---|---|---|
| Calculated (%) | 67.59 | 7.02 | 5.63 | 4.75 |
| Found (%) | 67.71 | 6.99 | 5.47 | 4.97 |

According to the above-mentioned synthesis procedures, other exemplified couplers (37)–(52) can be synthesized as well. Elementary analysis values of the thus synthesized couplers are as set forth in the following table:

| Exemplified compound No. | Calculated (%) | | | | Found (%) | | | |
|---|---|---|---|---|---|---|---|---|
|  | C | H | N | Cl | C | H | N | Cl |
| (37) | 60.37 | 5.70 | 8.80 | — | 60.09 | 5.69 | 8.89 | — |
| (38) | 61.43 | 6.07 | 8.43 | — | 61.27 | 6.10 | 8.39 | — |
| (39) | 64.50 | 7.22 | 6.27 | 5.29 | 64.67 | 7.15 | 6.41 | 5.11 |
| (40) | 66.99 | 5.82 | 7.10 | — | 67.12 | 5.61 | 7.23 | — |
| (41) | 63.70 | 4.17 | 8.28 | — | 64.01 | 4.12 | 8.39 | — |
| (42) | 65.56 | 4.95 | 7.65 | — | 65.52 | 4.91 | 7.75 | — |
| (43) | 67.82 | 7.13 | 5.53 | 4.66 | 67.79 | 7.16 | 5.41 | 4.79 |
| (44) | 64.93 | 7.27 | 7.21 | — | 65.02 | 7.21 | 7.15 | — |
| (45) | 71.03 | 6.63 | 5.52 | — | 70.87 | 6.59 | 5.69 | — |
| (46) | 64.94 | 7.47 | 6.14 | 5.18 | 64.91 | 7.42 | 6.31 | 5.23 |
| (47) | 53.15 | 5.17 | 6.53 | 16.52 | 53.00 | 5.21 | 6.48 | 16.37 |
| (48) | 73.46 | 4.52 | 5.71 | — | 73.31 | 4.49 | 5.83 | — |
| (49) | 68.24 | 7.29 | 5.43 | 4.58 | 68.31 | 7.27 | 5.40 | 4.71 |
| (50) | 67.59 | 7.02 | 5.63 | 4.75 | 67.71 | 6.89 | 5.47 | 4.87 |
| (51) | 60.12 | 6.56 | 3.51 | — | 60.27 | 6.52 | 3.65 | — |
| (52) | 68.09 | 8.35 | 6.11 | — | 68.27 | 8.32 | 6.17 | — |

Another class of the yellow couplers according to the present invention can be represented by the following general formula (III)

wherein A is as defined before, and Q' is a group of the formula

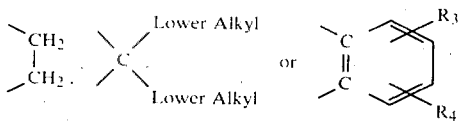

wherein $R_3$ is a hydrogen or halogen atom or an alkoxy group and $R_4$ is a hydrogen or halogen atom, an amino, acylamino, ureido, lower alkyl, alkoxy or hydroxy group.

Typical examples of the couplers (III) according to the present invention are illustrated below without limiting the scope of the present invention thereto.

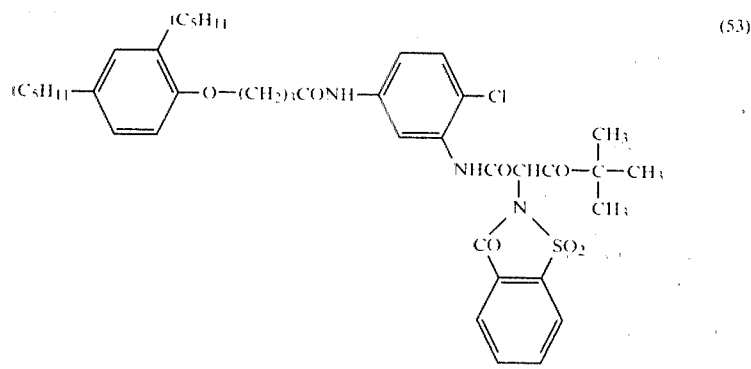

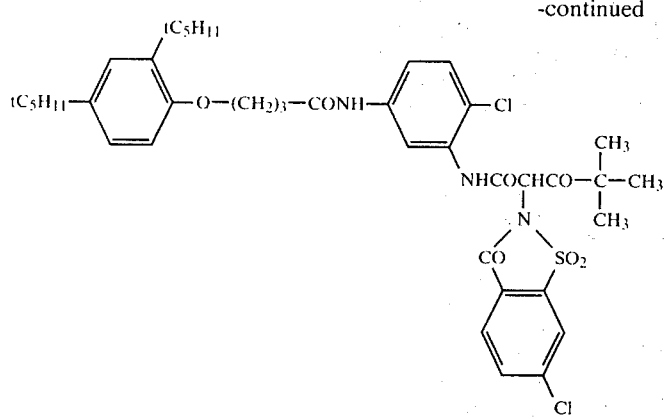

(54)

(55)

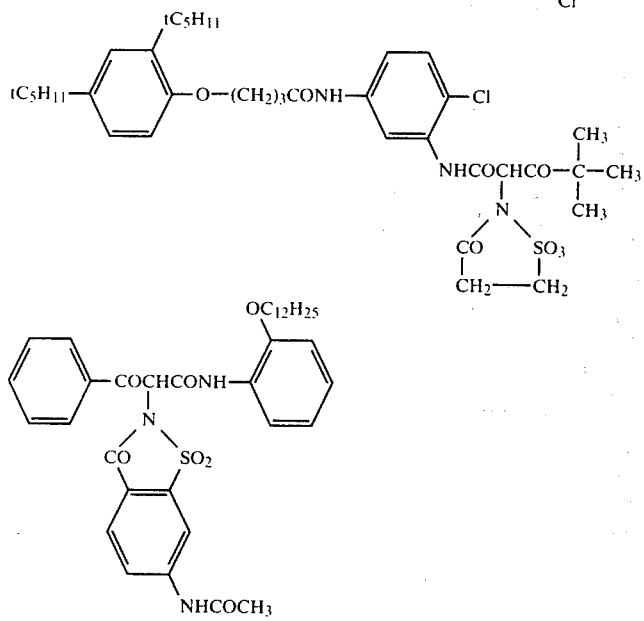

(56)

The thus-obtained yellow couplers according to the present invention are useful as the so-called protect type couplers used in the form of solutions in high boiling organic solvents, e.g. dibutyl phthalate, tricresyl phosphate, etc., which have a boiling point of more than 175° C. and which are difficultly miscible with water. Alternatively, they may be used in the form of solutions not in the above-mentioned high boiling organic solvents but only in substantially water-insoluble low boiling organic solvents such as ethyl acetate, butyl acetate, etc., or in water-soluble low boiling organic solvents such as methanol, ethanol, methyl isobutyl ketone, etc. Some of the couplers are quite useful as the so-called Fischer's type couplers which are dispersed by use of alkaline methanol or aqueous solutions. Further, they are useful as external couplers of such a type that the couplers are incorporated into developers to form dye images, or as couplers for use in the so-called diffusion transfer method in which a light-sensitive layer and an image-receiving sheet are brought into contact with each other during development to carry out image transfer.

Thus, the couplers according to the present invention may be used to form yellow dye images by application of various methods. Further, they have such advantages that even when any method is applied, the resulting dyes are excellent in spectral absorption characteristics and are quite stable to light, heat and humidity. In case the yellow couplers according to the present invention are incorporated into light-sensitive color photographic materials, the light-sensitive layers can be made thinner, whereby the photographic materials are enhanced in sharpness or improved in developability. In addition, the photographic materials incorporated with the couplers according to the present invention have such advantages that even when the development time is prolonged, they are not increased in fog, and form no such color stains as observed in the case where the conventional couplers are used.

As color developing agents which are used in combination with the couplers according to the present invention, there may be used p-aminophenol type developing agents whose amino groups have not been substituted, or phenylenediamine type developing agents such as, for example, diethyl-p-phenylenediamine hydrochloride, monomethyl-p-phenylenediamine hydrochloride, dimethyl-p-phenylenediamine hydrochloride, 2-amino-5-diethylaminotoluene hydrochloride, 2-amino-5-(N-ethyl-N-dodecylamino)-toluene, N-ethyl-N-$\beta$-methanesulfonamidoethyl-3-methyl-4-aminoaniline hydrochloride, N-ethyl-N-$\beta$-methanesulfonamidoethyl-4-aminoaniline and 4-N-ethyl-N-$\beta$-hydroxyethyl-aminoaniline. Some of the couplers according to the present invention are incorporated into an alkaline developer and are used as external couplers as mentioned previously. Even when the developer used in the above case contains sulfites, carbonates, bisulfites, bromides or iodides of alkali metals, the couplers according to the present invention bring about no detrimental interactions with the compounds contained in the developer. A typical example of the developer is as follows:

Color developing agent: 1–5 g.
Anhydrous sodium sulfite: 1–3 g.
Anhydrous sodium carbonate: 10–60 g.
Potassium bromide: 0.5–1.5 g.
Coupler: 1–30 g.
Water to make: 1,000 ml.

The couplers according to the present invention are also applicable to other light-sensitive color photographic materials susceptible to electromagnetic wave energy such as ultraviolet rays, visible rays, infrared rays, X-rays, γ-rays or micro-wave. In order to incorporate the couplers according to the present invention into light-sensitive photographic emulsions, there may be adopted any of the known procedures. For example, in order to be used as the previously mentioned protect type coupler, the coupler according to the present invention is dissolved in either one or both of at least one high boiling organic solvent having a boiling point of more than 175° C. such as tricresyl phosphate or dibutyl phthalate and at least one low boiling organic solvent such as ethyl acetate or butyl propionate. Subsequently, the resulting solution is mixed with an aqueous gelatin solution containing a surface active agent and then dispersed by means of a high speed rotary mixer or colloid mill to form a coupler dispersion. The thus formed coupler dispersion is added directly to a silver halide photographic emulsion, which is then coated on a support, followed by drying. Alternatively, the above-mentioned coupler dispersion is set and extruded to noodle form which is then freed from the low boiling solvent by water-washing or the like means and thereafter added to the photographic emulsion, which is then coated on a support, followed by drying. In this case, it is preferable, in general, to incorporate the coupler according to the present invention in a proportion of 10 to 300 g. per mole of the silver halide, though the proportion may be varied according to application purposes.

Among the 2-equivalent yellow couplers according to the present invention, the exemplified couplers (18), (19) and (20), (43) and (45), for example, may be dispersed in photographic emulsions by adoption of the above-mentioned procedure without using high boiling solvents; the exemplified couplers (13), (16), and (51), for example, may be dispersed in photographic emulsions by adding the alkaline methanol solutions of the couplers to said emulsions; the exemplified couplers (1), (3), and (37) for example, may be incorporated into developers; and the exemplified couplers (11), (14), and (52) for example, may be used for diffusion transfer since they form diffusing dyes.

The photographic emulsions used in the present invention may be prepared by use of various silver halides such as silver chloride, silver iodobromide, silver chlorobromide, etc. Further, the emulsions may be subjected to chemical sensitization or to optical sensitization using carbocyanine dyes or merocyanine dyes, and may have incorporated therein ordinary photographic additives such as, for example, antifoggants, stabilizers, anti-stain agents, anti-irradiation agents, physical property-modifying high polymer additives, film hardeners and coating aids.

Light-sensitive color photographic materials containing the couplers according to the present invention are incorporated with ultraviolet absorbers, whereby the resulting color images can be further enhanced in durability. Color developers which are used for exposed light-sensitive color photographic materials containing the couplers according to the present invention or those which have been incorporated with the couplers according to the present invention may contain development control agents, e.g. citrazinic acid and the like, in addition to the developing agent. Further, the photographic materials incorporated with the couplers of the present invention may be subjected to quick processing comprising, for example, color development, bleach-fixing, water-washing and stabilization. As the processing solution used in the above-mentioned bleach-fixing step, there has been known a solution containing as main ingredients an ethylenediamine tetraacetic acid iron salt and a thiosulfate such as, for example sodium thiosulfate or ammonium thiosulfate.

The present invention is illustrated in more detail below with reference to examples, but it is needless to say that the modes of practice of the present invention are not limited to the examples.

EXAMPLE 1

20.0 Grams of each of the exemplified couplers (7), (18), (21), (39), and (49) was completely dissolved at 60° C. in a mixture comprising 20 ml. of dibutyl phthalate and 60 ml. of ethyl acetate. The resulting solution was mixed with 10 ml. of a 6% aqueous solution of Alkanol B (alkylnaphthalene sulfonate produced by Du Pont) and with 200 ml. of a 6% aqueous gelatin solution, and the mixture was dispersed by means of a colloid mill to form a coupler dispersion. This coupler dispersion was added to 1 kg. of a high speed silver iodobromide emulsion, which was then coated on a film base and dried to obtain a light-sensitive photographic material having a stable film coating. The thus-obtained photographic material was exposed according to an ordinary procedure, and then developed at 20° C. for 10 minutes with a developer of the following composition:

N-Ethyl-N-β-methanesulfonamidoethyl-3-methyl-4-aminoaniline slfate: 5.0 g.
Anhydrous sodium sulfite: 2.0 g.
Benzyl alcohol: 3.8 g.
Sodium carbonate (monohydrate): 50.0 g.
Potassium bromide: 1.0 g.
Sodium hydroxide: 0.55 g.
Water to make up: 1,000 ml.

Subsequently, the developed photographic material derived from couplers (7), (18), and (21) was subjected to ordinary stop-fixing and bleaching treatments, while the developed photographic material derived from couplers (39) and (49) was subjected to 5 bath-treatments such as water-washing, stabilization, etc. Each sample obtained in the above manner was measured in absorption maximum (λ-max), maximum density (D-max) and storability of color developed image.

For comparison, control samples were prepared in the same manner as above, except that the couplers used were non-substituted type couplers identical in other structure with the couplers used in the above. The control samples were also measured in such photographic properties as mentioned above.

The results obtained in the above relative to couplers (7), (18), and (21) were as set forth in Table 1, while the results obtained in the above relative to couplers (39) and (49) were as set forth in Table 2.

TABLE 1

| Sample No. | Coupler | λ-max (mμ) | D-max | Ratio of residual dye (%) Light fastness | Ratio of residual dye (%) Humidity fastness |
|---|---|---|---|---|---|
| 1 | Non-substituted type coupler identical in other structure with the exemplified coupler (7) | 447 | 1.50 | 96 | 99 |
| 2 | Exemplified coupler (7) | 447 | 2.00 | 98 | 100 |
| 3 | Non-substituted type coupler identical in other structure with the exemplified coupler (18) | 452 | 1.80 | 75 | 97 |
| 4 | Exemplified coupler (18) | 452 | 2.30 | 75 | 99 |
| 5 | Non-substituted type coupler identical in other structure with the exemplified coupler (21) | 446 | 1.45 | 95 | 100 |
| 6 | Exemplified coupler (21) | 447 | 2.05 | 96 | 100 |

TABLE 2

| Sample No. | Coupler | λ-max (mμ) | D-max | Ratio of residual dye (%) Light fastness | Ratio of residual dye (%) Humidity fastness |
|---|---|---|---|---|---|
| 1 | Unsubstituted type coupler identical in structure with the exemplified coupler (39) | 447 | 1.21 | 95 | 99 |
| 2 | Exemplified coupler (39) | 447 | 1.91 | 96 | 99 |
| 3 | Unsubstituted type coupler identical in structure with the exemplified coupler (49) | 447 | 1.22 | 96 | 99 |
| 4 | Exemplified coupler (49) | 447 | 1.99 | 97 | 99 |

In Tables 1 and 2

λ-max: Spectral absorption maximum wavelength (mμ)
D-max: Maximum density
Ratio of residual dye: Ratio (%) of dye left after subjecting a portion having an initial density of 1.0 to the following treatments:

Treatments

Light fastness: Exposed to Xenon arc lamp at 50° C. for 30 hours.
Humidity fastness: Allowed to stand at 50° C. and RH 80% for 7 days.

From Table 1, it is understood that the couplers according to the present invention provide excellent properties and are quite useful as photographic yellow couplers for use in multi-layered and polychromatic photographic materials.

EXAMPLE 2

Using the exemplified couplers (7), (15), (19) and (46) and an non-substituted type couplers, i.e. a 4-equivalent coupler, identical in other structure with said couplers, Example 1 was repeated to prepare samples and a control sample, respectively.

These samples were individually measured by means of a densitometer in density of yellow dye to blue light at each stage. The results obtained were plotted to obtain the curves as shown in the accompanying drawing, in which the horizontal axis shows the exposure amount (log E) and the vertical axis shows the density. In the FIGURE, the curve 1 shows the case where the 4-equivalent coupler was used, and the curves 2, 3 and 4 show the cases where the exemplified couplers (7) and (46); (15); and (19) were used, respectively.

From the FIGURE, it is understood that the couplers according to the present invention can be successfully used even when silver is used in one half the amount required in the prior art.

EXAMPLE 3

Each of the exemplified yellow couplers (13), (16), and (51) was dispersed in a mixed solvent comprising ethanol and water, and then dissolved by addition of a 10% sodium hydroxide solution thereto. The resulting solution was mixed with a gelatin solution containing 12% of gelatin and 5.13% of Alkanol B, and then neutralized with acetic acid. The neutralized liquid was dispersed in a silver iodobromide emulsion, which was then coated on a support and dried to obtain a photographic material. This photographic material was subjected to ordinary exposure, and then developed with the same developer as in Example 1. Each sample prepared in the above manner was measured in λ-max and D-max.

For comparison, control samples were prepared in the same manner as above, except that the couplers used were non-substituted type couplers identical in other structure with the couplers used in the above. The control samples were also measured in such photographic properties as mentioned above.

The results obtained in the above for couplers (13) and (16) were as set forth in Table 3; and the results obtained in the above for coupler (51) were as set forth in Table 4.

TABLE 3

| Coupler | Fog | λ-max | D-max |
|---|---|---|---|
| Non-substituted type coupler identical in other structure with the exemplified coupler (13) | 0.15 | 450 | 1.85 |
| Exemplified coupler (13) | 0.20 | 450 | 2.12 |
| Non-substituted type coupler identical in other structure with the exemplified coupler (16) | 0.10 | 447 | 1.90 |
| Exemplified coupler (16) | 0.13 | 447 | 2.10 |

In Table 3, the λ-max and D-max are same as in Tables 1 and 2.

As is clear from Table 3, the couplers according to the present invention provide excellent photographic properties even when used in the Fischer's dispersion method.

TABLE 4

| Coupler | Fog | λ-max | D-max |
|---|---|---|---|
| Exemplified coupler (51) | 0.27 | 450 | 2.07 |
| Unsubstituted type coupler identical in structure with the exemplified coupler (51) | 0.15 | 450 | 1.84 |

In Table 4, the λ-max and D-max are same as in Tables 1 and 2.

As is clear from Table 4, the coupler according to the present invention provides excellent photographic properties even when used in the Fischer's dispersion method.

EXAMPLE 4

An emulsion containing each of the exemplified yellow couplers (11), (14), and (52) was coated on a support and then dried to obtain a photographic material. Each photographic material thus obtained was exposed and then treated with an alkaline developer (pH 13) containing 2 g/l of $Na_2SO_3$ and 11 g/l of 4-N-ethyl-N-β-hydroxyethylaminoaniline. The resulting negative sheet derived from coupler (52) was closely contacted at 24° C. for 3 minutes while the resulting negative sheets derived from couplers (11) and (14) were closely contacted at 240° C. for 5 minutes with an image-receiving sheet containing dimethyl-β-hydroxy-ethyl-γ-stearamidopropylammonium dihydrogenphosphate (mordant agent). Thereafter, the image-receiving sheet was peeled off to find that the yellow dye formed had transferred to the dye receiving sheet to give an excellent positive image.

EXAMPLE 5

A silver iodobromide emulsion was coated on a support to prepare a photographic material. This photographic material was subjected to ordinary color development using an external developer of the composition shown below which contained each of the exemplified yellow couplers (1), (3), and (37).

2-Amino-5-diethylaminotoluate: 2.0 g.
Anhydrous sodium sulfite: 2.0 g.
Anhydrous sodium carbonate: 20.0 g.
Potassium bromide: 1.0 g.
Coupler: 2.0 g.
Water to make up: 1,000 ml.

Subsequently, the developed photographic material was measured in photographic properties.

For comparison, the same photographic material as above was treated in the same manner as above, except that the coupler in the external developer was each of non-substituted type couplers identical in other structure with the couplers used in the above, and then measured in photographic properties.

The results obtained relative to couplers (1) and (3) were as set forth in Table 5. The results obtained relative to coupler (37) were as set forth in Table 6.

TABLE 5

| Coupler | Fog | λ-max | D-max |
|---|---|---|---|
| Non-substituted type coupler identical in other structure with the exemplified coupler (1) | 0.04 | 443 | 1.50 |

TABLE 5-continued

| Coupler | Fog | λ-max | D-max |
|---|---|---|---|
| Exemplified coupler (1) | 0.06 | 442 | 2.01 |
| Non-substituted type coupler identical in other structure with the exemplified coupler (3) | 0.05 | 452 | 1.70 |
| Exemplified coupler (3) | 0.08 | 452 | 2.00 |

In Table 5, the λ-max and D-max are same as in Table 1.

As is clear from Table 5, the couplers according to the present invention are quite useful as external couplers, as well.

TABLE 6

| Coupler | Fog | λ-max | D-max |
|---|---|---|---|
| Exemplified coupler (37) | 0.17 | 443 | 1.99 |
| Unsubstituted type coupler identical in structure with the exemplified coupler (37) | 0.04 | 443 | 1.47 |

In Table 6, the λ-max and D-max are same as in Tables 1 and 2.

As is clear from Table 6, the coupler according to the present invention is quite useful as an external coupler, as well.

BRIEF DESCRIPTION OF THE FIGURE

The accompanying FIGURE shows the characteristic curves of densities to blue light of the yellow dyes formed in Example 2, in which the curve 1 is the characteristic curve in the case where the control coupler was used, and the curve 2 is the characteristic curve in the case where the coupler according to the present invention was used.

What we claim is:

1. A process for forming a yellow dye image, which comprises bringing a yellow coupler having the formula

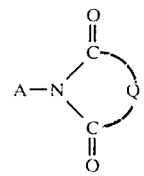

wherein A is a yellow coupler residue defined by removing one hydrogen atom of an active methylene group from a yellow coupler having the active methylene group; Q is a group having a formula

wherein Z is a hydrogen atom or an alkyl, aryl or aralkyl group; into contact with exposed silver halide crystals in the presence of a color developer for said silver halide crystals.

2. A light-sensitive silver halide color photographic material having a support and coated thereon a light-sensitive silver halide emulsion layer, containing a photographic yellow coupler of the formula

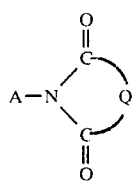

wherein A is a yellow coupler residue defined by removing one hydrogen atom of an active methylene group from a yellow coupler having the active methylene group; Q is a radical having a formula

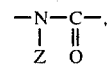

wherein Z is a hydrogen atom or an alkyl, aryl or aralkyl group.

3. A color developer for developing exposed light-sensitive silver halide color photographic material, which comprises a p-phenylenediamine type developing agent and a photographic yellow coupler according to claim 2.

* * * * *